United States Patent [19]

Kydonieus et al.

[11] 4,198,782
[45] Apr. 22, 1980

[54] CONTROL OF AGRICULTURAL PESTS BY CONTROLLED RELEASE PARTICLES

[75] Inventors: Agis F. Kydonieus; Seymour Hyman, both of New York, N.Y.

[73] Assignee: Herculite Protective Fabrics Corporation, New York, N.Y.

[21] Appl. No.: 881,961

[22] Filed: Feb. 27, 1978

Related U.S. Application Data

[63] Continuation of Ser. No. 722,235, Sep. 10, 1976, abandoned.

[51] Int. Cl.$^2$ .................. A01B 79/02; A01C 1/00; A01M 1/00; A01N 17/00
[52] U.S. Cl. .................................. 47/58; 43/124; 47/DIG. 5; 47/DIG. 9; 71/64 F; 111/1; 111/10; 424/16
[58] Field of Search .................. 424/16, 17, 19, 21, 424/23, 29, 11, 14, 26, 33, 83; 43/124, 131; 71/64 F, 3; 47/1.5, 23, 24, 25, 36, 48.5, 58, 74, DIG. 4, DIG. 5, DIG. 7, DIG. 13, DIG. 9; 106/15 AF; 111/1, 10

[56] References Cited

U.S. PATENT DOCUMENTS

| | | | |
|---|---|---|---|
| 2,956,922 | 10/1960 | Garber | 424/26 |
| 3,426,473 | 2/1969 | Cardarelli | 43/131 |
| 3,497,990 | 3/1970 | Jeffries | 43/131 |
| 3,581,686 | 6/1971 | Raymond | 111/1 |
| 3,605,321 | 9/1971 | Lazarus | 43/131 |
| 3,629,390 | 12/1971 | Wentworth | 43/131 |
| 3,705,938 | 12/1972 | Hyman et al. | 424/19 |
| 3,748,115 | 7/1973 | Sommer et al. | 71/64 F |
| 3,857,934 | 12/1974 | Bernstein et al. | 47/23 X |
| 3,864,468 | 2/1975 | Hyman et al. | 424/29 X |
| 4,002,458 | 1/1977 | Hofacker | 71/64 F |
| 4,021,364 | 5/1977 | Speiser et al. | 424/33 |
| 4,041,151 | 8/1977 | Milionis et al. | 424/33 |

FOREIGN PATENT DOCUMENTS

| | | |
|---|---|---|
| 2411373 | 11/1975 | Fed. Rep. of Germany ........... 424/20 |
| 1233418 | 5/1971 | United Kingdom . |
| 1281716 | 7/1972 | United Kingdom . |
| 1287749 | 9/1972 | United Kingdom . |
| 1299746 | 12/1972 | United Kingdom . |
| 1326825 | 8/1973 | United Kingdom . |

OTHER PUBLICATIONS

Laurie, A. et al., 1969, "Diagnosing Plant Disorders", *Commercial Flower Forcing,* pp. 223-227, McGraw-Hill Book Co.
Johnson, O., 1972, "'72 Pesticide Report", *Chemical Week,* pages showing Diazinon and Thimet (Phorate) from Jun. 21, and Jul. 26, issues only.
Stecher, R. G., (Ed.) 1968, *The Merck Index,* pp. 822, 342, Merck & Co. Inc., Rahway, N.J.

*Primary Examiner*—Edgar S. Burr
*Assistant Examiner*—James R. Feyrer
*Attorney, Agent, or Firm*—Sughrue, Rothwell, Mion, Zinn and Macpeak

[57] ABSTRACT

A method for the control of agricultural pests such as insects which comprises the application of polymeric particles which release an agent in a controlled manner. The particles can be applied to plants, seeds, soil or to the surface of the soil.

30 Claims, 4 Drawing Figures

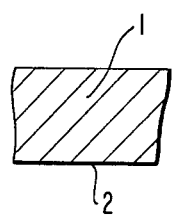
FIG 1
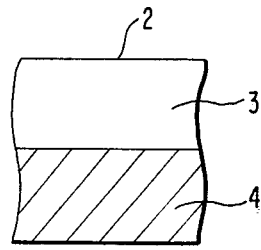
FIG 2
FIG 3
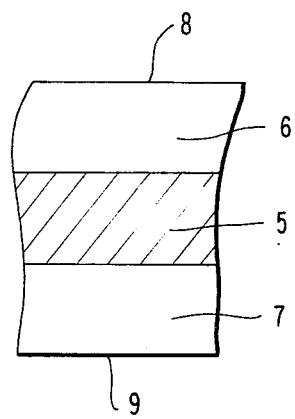
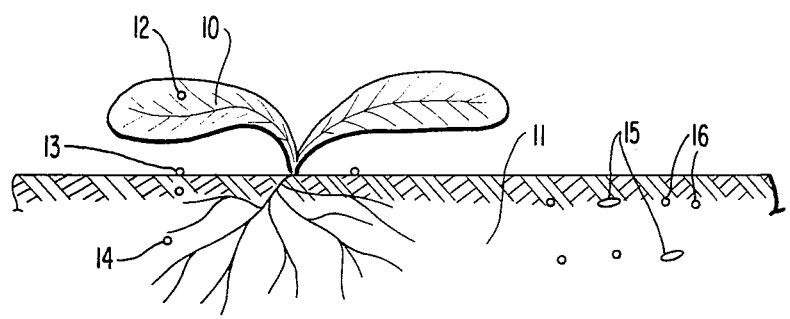
FIG 4

CONTROL OF AGRICULTURAL PESTS BY CONTROLLED RELEASE PARTICLES

This is a continuation, of application Ser. No. 722,235, filed Sept. 10, 1976, now abandoned.

BACKGROUND OF THE INVENTION

Increased scrutiny of the effects of various pesticides and other chemical agents has placed a greater emphasis on the utilization of already widely known agents whose effects have been studied over the years. Current federal regulations have slowed the development of new active agents such that it may take upwards of several years to bring to the marketplace a new and more effective agent that will meet the imposed governmental standards. In addition to the increased developmental time required, costs have also risen whereby development costs for a new pesticide in 1967 were $3.4 million, the cost has now risen to $8 million.

In view of the above, it is increasingly attractive to effectively utilize known agents for the control of agricultural pests. This could be done by decreasing the influence of environmental factors such as heat, humidity and rain upon the agent. Further, a desirable end result would be the extension of the active life of the agent in order to decrease the number of applications of the agent. A still further desirable end result would be the maintenance of the activity of the agent at a steady level such that the initial application activity would not be dangerously high followed by a period of the proper level followed by a period of low activity.

SUMMARY OF THE INVENTION

In order to provide an efficient delivery system for various agents for the control of agricultural pests, a method has been developed whereby polymeric particles which release the agent in a controlled manner are applied to the environment of a plant or seed. The particles can be applied to the agricultural environment such that the absolute amount of agent per unit area is the same as that applied by previous delivery methods. However, distinct and important advantages are gained by the use of the present invention whereby the effective life of the agent is extended. This factor may result in a lowering of the absolute amount of agent applied to the environment to achieve the same degree of agricultural pest control.

DESCRIPTION OF THE DRAWINGS

FIG. 1 indicates a cross-section of a polymeric granule 1 having in admixture therewith an active agent which can migrate to a surface 2.

FIG. 2 indicates a cross-section of a multilayered polymeric granule wherein an interior layer 4 is laminated to an exterior layer 3, wherein layer 4 contains an active agent in admixture which migrates through layer 3 to become available at its surface 2.

FIG. 3 shows a cross-section of a three-layered laminated granule wherein layer 5 contains an active agent which migrates through one or both of polymeric layers 6 and 7 to become available at one or both of surfaces 8 and 9, respectively.

FIG. 4 indicates plant 10 placed in soil 11 wherein granules have been applied to the plant, granules 13 have been applied to the soil surface and granules 14 are admixed with the soil. Further shown are seeds 15 which have been planted with granules 16.

DETAILED DESCRIPTION OF THE INVENTION

In the context of the present invention, the term "active agent" is intended to include or refer to substances capable of migrating or issuing into and through the polymeric materials used in the invention and to diffuse, evaporate or otherwise become available on, at or from the surface of said polymeric substances to which the agents have migrated. The term "migration" indicates a mass transfer or diffusion in molecular form of material through a solid, non-porous polymeric layer or material and excludes bulk transfer through pores or micropores. The active agents themselves are materials capable of killing or affecting agricultural pests such that damage to the crop is lessened.

Although the process of the present invention is especially effective in controlling insects, the term "pest" is intended to include animals and all other lower forms of life undesirable in the context of the invention from an agricultural standpoint including mammals, birds, vertebrates, invertebrates, worms, fungi, molds, protozoa, viruses, bacteria and other organisms capable of reproducing or multiplying.

The particles used in the method of the present invention can be of the laminated or the non-laminated polymeric varieties.

The laminated polymeric variety preferably has three or more layers. Thus, particles of the general structures described in U.S. Pat. Nos. 3,705,938 and 3,864,468 can be used in the method of the present invention. The particles can be formed by chopping, dicing or otherwise granulating laminated sheeting materials wherein the active agent is preferably contained in an interior "reservoir-type" layer and is capable of migrating through one or both of the outermost layers to become available on one or more surfaces of the particle.

The polymeric laminated sheeting to be granulated is preferably formed by providing a first sheet of a polymer which is substantially non-porous and can be virtually any polymeric material which is capable of being formed into a self-supporting continuous sheet or film. This first sheet, which is non-porous but not necessarily impervious to migration of the agent, can virtually be any of the available polymer sheeting materials such as various hydrocarbon polymers, such as rubber, and olefins, for example, polyethylene and polypropylene, imide, amide, ester, urethane, carbonate, cellulosic, halocarbon, ionomer, vinyl, such as polyvinyl chloride, polyvinylidene chloride, polyvinyl acetate and other polymers as well as their blends, interpolymers and copolymers. Polyvinyl chloride films are especially useful in preparing the sheeting to be granulated for the invention. While thicknesses of the sheet material is not critical, and articles of about 0.100 inches thick can be produced, excellent results have been obtained with single sheets having a thickness of about 0.015 inches and with multi-ply laminates having a combined thickness of about 0.030 inches.

To the first sheet, a polymeric liquid composition containing the active agent is applied. Although any liquid composition capable of being set to form a solid film of plastic on the surface of the first sheet can be used, the term should be understood to include plastisols, polymer solutions, polymer-in-liquid emulsions and 100% solids liquid polymers.

The laminate may be completed by the application of a second polymeric sheet to the liquid composition followed by a lamination step to form an integral laminate which can then be chopped, diced or otherwise granulated to produce the particles for use in the method of the present invention. Additional control of the release of the agent can be accomplished by the use of a "blocking" layer whereby the agent is slowed or stopped in its migration through the layer. Additional embodiments of this laminated variety include a structure whereby two agents are included in one or more "reservior-type" layers. Thus, a structure could be formulated whereby one agent migrates to one surface while another agent migrates to the opposite surface with a barrier layer between two reservoir layers containing the respective agents. Thus, laminated structures such as those described in pending application Ser. No. 535,658, now abandoned, which corresponds to Belgium Pat. No. 807,146, of which one of the inventors of the present application is a co-inventor, can be used as the sheeting to be granulated.

Although the laminated sheetings are useful in a wide variety of thicknesses, a three-layered laminate is preferred wherein the outer layers have a thickness on the order of from about 1 to 10 mils, the polymeric core layers have a thickeness on the order of from about 2 to about 20 mils and the overall laminates have a total thickness of up to about 50 mils.

Non-laminated sheeting which can be comminuted to provide controlled release particles include strips, tapes and films of solid, polymeric materials, usually thermoplastics, into which effective amounts of the agent may be blended by milling or other processes such as extrusion.

The agents to be used in the present invention include those general classes of materials presently utilized to control agricultural pests and which are capable of migration through the polymeric particles. These general classes can include insecticides, rodenticides, acracides, nematocides, moluscides, anthelmintic substances, insect, bird and animal repellants, fumigants, algicides, insect growth regulators, antimetabolites, chemosterialants, juvenile hormones, analogs and mimics; and such pest foods and food mimics, any of the foregoing of which are capable of "migration", as defined above. Active agents used in the dispensers described in application U.S. Ser. No. 400,548, now abandoned, and corresponding to Belgium Pat. No. 820,284 of which one of the present co-inventors was the inventor, can be used in the particles used in the method of the present invention. Especially preferred active agents include Diazinon, which is O,O-diethyl-O(2-isopropyl-6-methyl-4-pyrimidyl)phosphorothioate, and Thimet which is a trademark for a systemic insecticide based on O,O-diethyl-S-(ethylthiomethyl)phosphorodithioate.

In general, the particles of the present invention can be applied in an amount corresponding to the same amount of the active agent which is applied to that particular crop in a non-controlled release form. Lower amounts may be applied if found to be adequate in controlling the particular pest while higher amounts may be used in view of the lowered danger in view of the present invention, of the application of too high a concentration.

Additional agents or materials can be formulated in the particles of the present invention as an integral part of the particle itself or intermixed therewith. Thus, the outer layer of the laminate or non-laminated particle itself may contain fillers, pigments, ultraviolet screening agents or other standard materials used in polymer technology.

Although release rates may vary according to the particular polymer and/or agent used, such rates can be easily determined by one of ordinary skill in the art and the release rates can be programed either for the entire growing season of the crop or for the life cycle of the particular pest infestation. The present invention allows for a unique maximization of effectiveness of the agent and can result in the elimination of costly over-spraying which is particularly advantageous where extremely toxic chemicals are used or where crop growth or timing makes it impractical to return to the crop fields for additional application.

The method of the present invention is effective in controlling agricultural pests by application of the particles to the environment where control is desired. Thus, the particles can be applied to the soil environment of a plant or seed, at the surface, intermixed throughout or primarily at a desired depth, to the plant itself or to the seed as an admixture with the seeds before planting or in the furrow or hole provided for the seed.

The following Reference Example is provided to demonstrate the preparation of a laminated sheeting which can be granulated to obtain the particles used in the present invention.

REFERENCE EXAMPLE

A sheet of polyvinylchloride (PVC) film having a thickness of 0.004 inch was coated with a plastisol coating prepared by dispersing 100 parts of polyvinylchloride resin in about 25 parts of dioctylphthalate and then dispersing 120 parts of chlorpyrifos, i.e. O,O-diethyl O-(3,5,6-trichloro-2-pyridyl) phosphorothioate, into the 125 parts of plastisol. The plastisol thus prepared was mixed until uniform and the coating was applied to the base sheet of polyvinylchloride in a thickness of about 0.02 inches. The coated polyvinylchloride film was then overlaid with a second sheet of polyvinylchloride also having a thickness of 0.004 inches. The assembled layers were then laminated under suitable conditions of heat and pressure until an integral firmly bonded product was obtained. The laminated structure thus produced contained approximately 30.8% chlorpyrifos insecticide based on the total weight of the laminate.

The following experiments indicate the utilization of particles formed from laminated sheets similar to the one described in this Reference Example.

EXAMPLE 1

A laminated sheet was prepared as in the Reference Example with the substitution of the chlorpyrifos by the insecticide Diazinon such that the Diazinon comprised 6% by weight of the total laminated sheet. The sheet was then chopped into small granules and its effectiveness was compared with standard Diazinon 14G granules.

The polymeric laminated granules (hereinafter referred to as HERCON granules) and the standard Diazinon 14G granules were weighed to the correct rate and placed with 500 cubic centimeters of air-dried top soil in a plastic bag and shaken vigorously until a homogeneous mixture was obtained. 25 milliliters of water were added and mixed to obtain a further homogeneous mixture. The treated soil was split into 250 cubic centimeter aliquots and placed in 16-ounce wax-coated paper cups. 10 kernels of germinated corn were planted 1.5 centimeters deep in each cup and 10 four- to seven-day old *Diabrotica balteata* larvae were placed on the soil surface. The cups were sealed with a snap-on plastic lid and held at room temperature for 7 days at which time the soil was sifted through a No. 16 sieve having 1.19 millimeter openings to recover the larvae and determine their mortality. The soil was retained and placed in plastic bags to which 12.5 milliliters of water were added. After a thorough mixing, the soil was placed in paper cups and retested as above. Each treatment was replicated two times to yield 4 cups for a total of 40 larvae for each treatment.

As shown in Table A, at the rate of 1 part per million, the polymeric laminated HERCON Diazinon 6G and the standard Diazinon 14G were effective at least 5 weeks. However, at the rate of 2 parts per million, the HERCON Diazinon 6G was effective for 13 weeks while the standard Diazinon 14G was effective for only 7 weeks. Thus, as can be seen by the following Table A, the use of the present invention increased the duration of effectiveness of Diazinon by almost 100% at a substantially lower concentration.

TABLE A

Percent Mortality of *Diabrotica balteata* Larvae Held in Field Soil Treated With Diazinon In HERCON ® And Standard Formulations

| Treatment | Rate ppm | Percent Mortality at Indicated Week | | | | | | | |
|---|---|---|---|---|---|---|---|---|---|
| | | 1 week | 3 week | 5 week | 7 week | 9 week | 11 week | 13 week | 15 week |
| Diazinon-HERCON | 1 | 90 | 100 | 90 | 70 | 75 | 60 | 45 | 0 |
| 6.0% | 2 | 75 | 100 | 90 | 100 | 80 | 95 | 80 | 35 |
| (GA-4-587) | 4 | 85 | 95 | 100 | 100 | 100 | 95 | 100 | 95 |
| Diazinon 14G | 1 | 75 | 90 | 80 | 60 | 30 | 25 | 25 | 0 |
| | 2 | 90 | 100 | 100 | 95 | 50 | 30 | 20 | 10 |
| | 4 | 100 | 85 | 70 | 95 | 100 | 85 | 90 | 30 |
| Check #1 | — | 15 | 35 | 0 | 20 | 25 | 25 | 30 | 0 |
| Check #2 | — | 10 | 25 | 15 | 15 | 5 | 25 | 20 | 5 |

EXAMPLE 2

This experiment was conducted in order to evaluate the effectiveness of the present invention wherein the controlled released particles are introduced to the environment of seeds during planting.

Standard greenhouse pots were filled to within about 5 centimeters (cm) of the top with soil. Insect control dispensers containing Thimet where then applied to the soil surface on a 7.5 cm line in the center of the soil surface. In addition to dispensers without Thimet and control pots, pots were prepared with controlled release particles according to the present invention and with standard Thimet 15G Attapulgite clay granules, attention being paid to the absolute amount of Thimet actually applied to each pot via the different delivery systems. Thereafter, 3 field corn seeds were placed on the treatment near the centers of the pots and the pots were then covered with about 2.5 cm of soil, placed in a greenhouse and watered for good germination and growth. The plants were carefully thinned to one plant per pot when the plants were 5 to 7 cm tall.

When the corn plants were 15 to 18 cm tall in about 17 days, the soil in each pot was lightly cultivated and 10 southern corn rootworm larvae (3rd instar) were placed on the soil adjacent to each corn plant. Feeding damage to the corn was classified as follows:

0 = no feeding
1 = slight feeding
2 = moderate feeding
3 = severe feeding

Seven to 10 days following each damage rating, a new seeding of corn was carefully made in the same location as the original planting. This regime was followed for the duration of the experiment.

As shown below in Table B, the method of the present invention utilizing controlled released polymeric particles gave good control against the southern rootworm (*Diabrotica undecimpunctata howardii* Barker) for 164 days when the experiment was completed. The standard formulation of Thimet designated as Thimet 15G at the same rate of 7.5 milligrams (mg) was only effective for 73 days and completely ineffective thereafter. To obtain the same effectiveness as the controlled release dispenser, one would have to use 4 to 8 times as much Thimet in the form of the standard Thimet 15G formulation.

TABLE B

Control of Sourthern Corn Rootworm With Thimet Dispenser From H-1 And Attapulgite Clay Granules

| Treatment System | Rate ai Thimet (Mg) | Average Corn Damage Rating (Days After Treatment) | | | | | |
|---|---|---|---|---|---|---|---|
| | | 17 | 42 | 73 | 94 | 122 | 164 |
| H-1 | — | 3.0 | 3.0 | 3.0 | 3.0 | 3.0 | 3.0 |
| Clay | 7.5 | 1.0 | 0.7 | 0.3 | 3.0 | 3.0 | 3.0 |
| | 15.0 | 1.0 | 0.0 | 0.0 | 2.3 | 3.0 | 3.0 |
| | 30.0 | 0.0 | 0.0 | 0.0 | 0.0 | 0.7 | 1.7 |
| | 60.0 | 0.0 | 0.0 | 0.0 | 0.7 | 0.0 | 0.0 |
| H-1 | 7.5 | 0.7 | 0.3 | 0.0 | 1.0 | 0.3 | 0.0 |
| | 15.0 | 0.7 | 0.0 | 0.0 | 0.0 | 0.0 | 0.0 |
| | 30.0 | 1.0 | 0.0 | 0.0 | 1.3 | 0.7 | 0.0 |
| | 60.0 | 0.0 | 0.0 | 0.0 | 0.0 | 0.0 | 0.0 |
| Control | — | 3.0 | 3.0 | 3.0 | 3.0 | 3.0 | 3.0 |

EXAMPLE 3

In order to determine the effect of the Thimet to the actual corn plants themselves utilized in Example 2 above, the systemic characteristics of the plants were determined.

When the corn plants of Example 2 were 15 to 18 cm tall, the second leaf from the bottom was excised for bioassay with the western potato leafhopper (*Empoasca abrupta* DeLong). The rates for both delivery systems were 7.5, 15, 30 and 60 mg of actual Thimet present.

As shown in Table C below, the controlled release formulation in accordance with the present invention at the rate of 7.5 mg was 100% effective for 124 days when the experiment was discontinued. The standard Thimet 15G clay formulation gave 100% control for only 45 days with no control thereafter. To obtain the same control with the standard clay formulation, 4 to 8 times more actual Thimet would have to be applied to the soil.

TABLE C

Systemic Control Of Western Potato Leafhopper With Thimet Dispensed From H-1 And Attapulgite Clay Granules

| Treatment System | Rate ai Thimet (Mg) | Average % Control of Leafhoppers (Days After Treatment) | | | | |
|---|---|---|---|---|---|---|
| | | 24 | 45 | 73 | 96 | 124 |
| H-1 | — | — | 100* | 0.0 | 33 | 0.0 |
| Clay | 7.5 | 100 | 100 | 0.0 | 0.0 | 0.0 |
| | 15.0 | 100 | 100 | 100 | 66 | 0.0 |
| | 30.0 | 100 | 100 | 100 | 66 | 100 |
| | 60.0 | 100 | 100 | 100 | 100 | 100 |
| H-1 | 7.5 | 100 | 100 | 100 | 100 | 100 |
| | 15.0 | 100 | 100 | 100 | 100 | 97 |
| | 30.0 | 100 | 100 | 100 | 100 | 100 |
| | 60.0 | 100 | 100 | 100 | 100 | 100 |
| Control | — | 0.0 | 0.0 | 0.0 | 0.0 | 0.0 |

*Probably an artifact.

EXAMPLE 4

This experiment was conducted in order to determine the comparative efficiency of Diazinon dispensers within and outside of the scope of the present invention against sweet corn borers.

Sweet corn was sown in small plots at fortnightly intervals. After the corn plants were 3 weeks old, Diazinon insecticide was spread by hand on the plants at the rate of 30 kilograms per hectar. The controlled release particles of the present invention were 3-layered particles containing 10% by weight Diazinon while the standard particles were 10% Diazinon calcite granules.

At various intervals after the insecticide treatment, one day old larvae of sweet corn borers (*Sesamia nonagrioides*) were placed on the plants. Since the granular materials tend to collect at the leaf axils, the larvae were placed at these axils at the rate of 30 larvae per plant. Ten days after infestation, the plants were uprooted and examined in the laboratory. The examinations consisted of counting the number of live larvae which had penetrated into the plant.

Table D below summarizes the results utilizing the standard 10% Diazinon calcite granules as opposed to the controlled release dispensers according to the present invention (below designated as "HERCON L 53-28-2"). At four different infestation dates, the controlled release particles according to the present invention gave good control and were superior to the conventional granules. Although both materials were very effective when the larvae were placed on the plant one day after treatment, an increase in the rate of live larvae was observed one week after treatment, primarily on plants treated with the conventional granules. It should be noted that 20 days after treatment the rate of live larvae on the plants treated with either formulation was lower than for the control plants. After 20 days, the number of larvae on the plants treated with the controlled release particles were of the same level as the number of larve on the plants treated with the standard calcite formulation only one week from the date of initial treatment. It should also be noted that the controlled release formulation was not phytotoxic even at high temperatures of 40° C. and at a very high relative humidity of 80 to 90%.

TABLE D

Control Of S. Nonagriodies From HERCON ® Dispensers And Calcite Granules

| | (Days After Treatment) | | | |
|---|---|---|---|---|
| | 1 | 7 | 14 | 20 |
| Treatment | No. Of Larvae Per 10 Plants | No. Of Larvae Per 10 Plants | No. Of Larvae Per 10 Plants | No. Of Larvae Per 10 Plants |
| HERCON L 53-28-2 | 0 | 16 | 16 | 46 |
| Diazinon 10% | 1 | 50 | 60 | 75 |
| Check | 96 | 185 | 120 | 122 |

EXAMPLE 5

This experiment was conducted in order to evaluate granular form Diazinon insecticide according to the present invention with a standard formulation as they affect corn plant tolerances and corn silage yields at harvest when applied to the furrow at seed planting when exposed to northern corn rootworm larvae.

Insecticidal granules were placed with corn seeds into plowed and fitted soil to result in an in-furrow treatment. The standard insecticidal granules were the Diazinon 14G granules used in Example 1. The controlled release particles were 3-layered Diazinon formulations as previously described. Root ratings obtained from 10 plants per replicate (3 replicates) were placed on the Iowa State University System, utilizing a scale from 1 to 6 as indicated below:

1 = no feeding damage
2 = feeding scars present
3 = at least one root pruned
4 = at least one full root node pruned
5 = at least two full root nodes pruned
6 = at least three full root notes pruned In order to qualify as a pruned root, the root must have been pruned to within 1½ inches of the plant. Brace roots are considered as a node if they are below the soil surface.

As indicated below in Table E, the controlled release formulations according to the present invention gave average root rating damage indices and average silage yields which were superior to the utilization of the standard granular Diazinon 14G from Example 1. All formulations, both controlled release and standard, outyielded the untreated check value in silage gain.

TABLE E

Root Ratings And Yields Obtained In The NCR Control Study With Experimental Insecticides

| Material | Rate lbs. ai/A | Amount/Plot (1/1000 A) | Index of Phytotoxicity* | Average Root Ratings Damage Index** | Average Silage Yields Tons/Acre at 32% DM |
|---|---|---|---|---|---|
| HERCON Diazinon 11.3 G | 1 | 4.53 G | 0 | 3.0 | 25.20 Tns |
| HERCON Diazinon 8.3 G | 1 | 5.89 G | 0 | 2.1 | 26.60 |
| Diazinon 14 G | 1 | 3.62 G | 0 | 3.4 | 24.50 |
| Untreated Check | — | — | 0 | 3.8 | 20.81 |

*Key for Phytotoxicity Index, 0 = none and 10 = 100% Kill.
**Obtained from 30 plant samples.

EXAMPLE 6

This experiment was conducted in order to compare the effectiveness of granular insecticides against cabbage maggots when the granules are applied in-furrow with the seeds.

The Diazinon 14G granules used in Example 1 and controlled release particles according to the present invention were applied to respective furrows during cabbage seed plantings. The granules were in the form of banded granules and were incorporated lightly by raking in 2 inch bands at a depth of ½ inch or less.

As indicated below in Table F, all of the granular insecticide treatments provided higher head yield weights than the untreated check plot. However, the furrows treated with the controlled release dispensers according to the present invention gave far more root protection from maggot tunneling than the standard Diazinon 14G.

TABLE F

Cabbage Root Maggot Control and Yields Obtained in Granular Insecticide In-Furrow Direct Seeded Cabbage Study

| Material | Rate lbs. ai/A | Amount Product Per A | Stand Phyto-toxicity | Total Root Maggot Damaged Plants Out of 30 (10 Per Rep) | % Clean Plants | Average Wt./Head |
|---|---|---|---|---|---|---|
| Diazinon 14 G | 1 | 7.0 lb. | 0 | 16 | 46.6 | 1.75 lbs. |
| HERCON 11.33% Diazinon | 1 | 9.5 lb. | 0 | 6 | 80.0 | 1.82 |
| HERCON 8.8% Diazinon | 1 | 12.0 lb. | 0 | 5 | 83.3 | 1.64 |
| Untreated Check | — | — | 0 | 18 | 40.0 | 1.40 |

Phytotoxicity Stand 0 = none, 10 = 100% kill.
Rated approximately one month post treatment.
Roots of 30 plants (10 per replicate) were dug, washed and roots examined for tunneling.
Yields represent average weights from 30 cabbage heads (10 per replicate) cut and weighed about 50 days after treatment.

While the invention has been described in detail and with reference to specific embodiments thereof, it will be apparent to one skilled in the art that various changes and modifications can be made therein without departing from the spirit and scope thereof.

What is claimed is:

1. A method for the control of agricultural pests comprising producing polymeric controlled insecticide release particles by granulating a laminated sheeting material comprising
   (i) a first solid, non-porous polymeric sheet having adhered thereto
   (ii) a polymeric core film containing an insecticide selected from the group consisting of Diazinon and Thimet, and having on the opposite side of the first sheet, adhered thereto
   (iii) a second solid, non-porous polymeric sheet
   said insecticide migrating by molecular migration through at least one of said sheets to become available on at least one surface of said particles; and applying said particles to a location where it is desired to control pests.
2. The method of claim 1, wherein said first and second sheets are sheets of polyvinyl chloride.
3. The method of claim 1, wherein said first and second sheets (i) and (iii) have a thickness of about 1 to 10 mils and said polymeric core film (ii) has a thickness of about 2 to about 20 mils.
4. The method of claim 1, wherein said molecular migration is other than by bulk transfer of said insecticide through pores or micropores.
5. The method of claim 1, wherein said insecticide is Diazinon.
6. The method of claim 1, wherein said insecticide is Thimet.
7. The method of claim 1, wherein said location is the environment of plants.
8. The method of claim 7, wherein said first and second sheets are sheets of polyvinyl chloride.
9. The method of claim 7, wherein said first and second sheets (i) and (iii) have a thickness of about 1 to 10 mils and said polymeric core film (ii) has a thickness of about 2 to about 20 mils.
10. The method of claim 7, wherein said molecular migration is other than by bulk transfer of said insecticide through pores or micropores.
11. The method of claim 7, wherein said insecticide is Diazinon.
12. The method of claim 7, wherein said insecticide is Thimet.
13. The method of claim 1, wherein said location is the surface of plants.
14. The method of claim 13, wherein said first and second sheets are sheets of polyvinyl chloride.
15. The method of claim 13, wherein said first and second sheets (i) and (iii) have a thickness of about 1 to 10 mils and said polymeric core film (ii) has a thickness of about 2 to about 20 mils.
16. The method of claim 13, wherein said molecular migration is other than by bulk transfer of said insecticide through pores or micropores.
17. The method of claim 13, wherein said insecticide is Diazinon.
18. The method of claim 13, wherein said insecticide is Thimet.
19. The method of claim 1, wherein said location is the environment of seeds.
20. The method of claim 19, wherein said first and second sheets are sheets of polyvinyl chloride.
21. The method of claim 19, wherein said first and second sheets (i) and (iii) have a thickness of about 1 to 10 mils and said polymeric core film (ii) has a thickness of about 2 to about 20 mils.
22. The method of claim 19, wherein said molecular migration is other than by bulk transfer of said insecticide through pores or micropores.
23. The method of claim 19, wherein said insecticide is Diazinon.
24. The method of claim 19, wherein said insecticide is Thimet.
25. The method of claim 1, wherein said location is the surface of seeds.

26. The method of claim 25, wherein said first and second sheets are sheets of polyvinyl chloride.

27. The method of claim 25, wherein said first and second sheets (i) and (iii) have a thickness of about 1 to 10 mils and said polymeric core film (ii) has a thickness of about 2 to about 20 mils.

28. The method of claim 25, wherein said molecular migration is other than by bulk transfer of said insecticide through pores or micropores.

29. The method of claim 25, wherein said insecticide is Diazinon.

30. The method of claim 25, wherein said insecticide is Thimet.

* * * * *